United States Patent [19]

Hirsch et al.

[11] Patent Number: 4,605,661

[45] Date of Patent: Aug. 12, 1986

[54] AROMASTASE INHIBITING α,α-DIARYLIMIDAZOLE-4(5)-PROPIONITRILES, α,α-DIARYLIMIDAZOLE-4(5)-PROPIONAMIDES, AND 4(5)-(2,2-DIARYLETHYL)IMIDAZOLES

[75] Inventors: Kenneth S. Hirsch, New Palestine; Richard P. Pioch, Indianapolis, both of Ind.

[73] Assignee: Eli Lilly and Company, Indianapolis, Ind.

[21] Appl. No.: 621,594

[22] Filed: Jun. 18, 1984

[51] Int. Cl.[4] .................. A61K 31/415; A61K 31/44; C07D 233/64; C07D 401/06
[52] U.S. Cl. ........................ 514/400; 514/341; 514/396; 546/278; 548/335; 548/342
[58] Field of Search ............... 548/342, 335; 546/278; 424/273 R, 263; 514/341, 396, 400

[56] References Cited

U.S. PATENT DOCUMENTS

| | | | |
|---|---|---|---|
| 4,235,893 | 11/1980 | Brodie et al. | 260/397.4 |
| 4,264,521 | 4/1981 | Pioch | 260/465 G |
| 4,281,141 | 7/1981 | Merrit et al. | 548/342 |
| 4,398,942 | 8/1983 | Ikari et al. | 71/92 |

FOREIGN PATENT DOCUMENTS 2101114 1/1983 United Kingdom ............... 548/335

OTHER PUBLICATIONS

Siiteri et al., *Handbook of Physiology-Endocrinology II*, Part 1, pp. 615–629.
Goodman and Gilman's *The Pharmacological Basis of Therapeutics*, 6th Edit., p. 1304 (1980).
Harris, Expl. Cell Biol., 53, pp. 1–8 (1985).
Brodie et al., Endocrinology, 100, pp. 1684–1695, (1977).
Coombes et al., Lancet, pp. 1237–1239 (Dec. 1, 1984).
Santen et al., Ann. Int. Med., 96, pp. 94–101 (1982).
Barone et al., J. Clin. Endocrin. and Metabol., 49(5), pp. 672–676 (1979).
Berkowitz et al., Amer. J. Epid., 121(2), pp 238–245 (1985).
Tseng et al., J. Clin. Endocrin. and Metabol., 55(5), pp. 1029–1031 (1982).

*Primary Examiner*—Richard A. Schwartz
*Assistant Examiner*—Kurt G. Briscoe
*Attorney, Agent, or Firm*—Robert A. Conrad

[57] ABSTRACT

This invention provides a method of inhibiting aromatase and treating or preventing estrogen-dependent diseases in mammals by administering certain imidazole derivatives. Pharmaceutical formulations of the imidazole derivatives and certain imidazoles are also provided.

18 Claims, No Drawings

AROMASTASE INHIBITING α,α-DIARYLIMIDAZOLE-4(5)-PROPIONITRILES, α,α-DIARYLIMIDAZOLE-4(5)-PROPIONAMIDES, AND 4(5)-(2,2-DIARYLETHYL)IMIDAZOLES

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see Cancer Research, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see Br. J. Cancer, 25, 270 (1971)). Two of the known aromatase inhibitors, testolactone and aminoglutethimide, have shown a beneficial effect in treatment of breast cancer. See Cancer Research, supra.

Endometriosis is characterized by an abnormal proliferation of the endometrium of the uterus. Since the endometrium is dependent on estradiol for its growth, an inhibitor of estrogen production should stop the progression of the disease.

Benigh breast disease, or often called fibrocystic breast disease, appears to be dependent on ovarian steroids. See Cancer, 49, 2534 (1982). Aromatase inhibitors have not been tried in this disease, but antiestrogens seem to be of benefit. See Obstet. Gynecol., 54, 80 (1979).

Polycystic ovarian disease is one of the most common causes of infertility in women. The disease appears to result from an abnormality in steroid metabolism, and the major form of therapy in this disease is the antiestrogen, clomiphene. See Clin. Endocrinol., 12, 177 (1980).

U.S. Pat. No. 4,281,141 describes the preparation and use of certain 3-(imidazol-4-yl)-2-phenyl-propanenitriles as agents useful in the control of powdery mildew of cultivated plants.

It is the purpose of this invention to provide certain imidazole derivatives, pharmaceutical formulations, and a method for inhibiting the enzyme aromatase in mammals employing certain imidazole derivatives. The invention thus provides for the treatment or prevention of breast cancer and other estrogen-dependent diseases.

SUMMARY OF THE INVENTION

This invention provides a method of inhibiting aromatase in mammals which comprises administering to said mammal an aromatase inhibiting amount of a compound of the formula

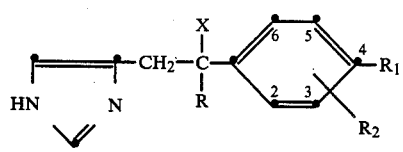

wherein
R is pyridyl or

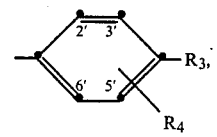

X is —CN, —CONH$_2$, or hydrogen, and
R$_1$, R$_2$, R$_3$, and R$_4$ are independently hydrogen, methyl, methoxy, fluoro, chloro, bromo, or trifluoromethyl, or a pharmaceutically acceptable salt thereof.

By virtue of their ability to inhibit the enzyme aromatase, the compounds of the above formula are useful in the treatment and prevention of estrogen-dependent diseases, especially breast cancer, in mammals.

Further provided by this invention are pharmaceutical formulations comprising one or more of the compounds of the above formula in combination with a suitable pharmaceutical carrier, diluent, or excipient therefor. The formulations provided by this invention are particularly useful in treating mammals suffering from estrogen-dependent diseases such as breast cancer.

In addition, this invention provides for the novel compounds of the above formula wherein X is —CONH$_2$ or hydrogen.

DETAILED DESCRIPTION AND PREFERRED EMBODIMENT

A preferred group of compounds useful in the method and formulations of this invention are those wherein:

(a) R$_1$ is fluoro or chloro, and
(b) R is phenyl (R$_3$ and R$_4$ are both hydrogen) or substituted phenyl, especially where R$_3$ is halo, especially chloro or fluoro, or trifluoromethyl.

The most preferred compound is α,α-bis(4-chlorophenyl)imidazole-4(5)-propionitrile and its pharmaceutically acceptable salts.

Most of the nitrile compounds used in this invention (X=—CN) and methods of making the compounds are disclosed in U.S. Pat. No. 4,281,141. Intermediates for preparing these compounds are claimed in U.S. Pat. No. 4,264,521. Both patents are expressly incorporated in this application by reference. The compounds as disclosed in the patents are described as being useful in controlling powdery mildew of cultivated plants. The patents do not disclose any utility for use in humans or any utility related to the inhibition of aromatase or the treatment of estrogen-dependent diseases. Other compounds of the present invention which are not expressly taught in the above references can be made by the same procedures using the appropriate starting materials.

The compounds of the above formula wherein X is —CONH$_2$ can be prepared from the corresponding nitrile compounds by any of a number of methods known in the art. A preferred method for their preparation consists of heating the nitrile compound at about 80°–100° C. in a solution of sulfuric acid or other strong acid for about 2–6 hours to provide the corresponding amide. The product may be purified by standard methods such as crystallization or high pressure liquid chromatography.

The compounds of the above formula wherein X is hydrogen can also be preparred from the nitrile compounds by decyanation procedures well known in the art. A preferred method consists of heating the nitrile compound with a Gringard reagent, such as ethyl magnesium bromide, in a non-reactive solvent such as toluene, hexane, or tetrahydrofuran. The two reagents are generally heated at temperatures from about 40° C. up to the reflux temperature of the reaction mixture. After 10–20 hours, the reaction is treated with acid and heated to provide the desired decyanated product which can be purified by standard methods. Other decyanation methods are known in the art as are other methods for preparing the compounds without going through the nitrile intermediate; see, e.g., P. A. J. Janssen in "Synthetic Analgesics", Pergamon Press, New York (1960), Chapter III, and references cited therein.

As will be recognized by those skilled in the art, except when the phenyl groups are identically substituted, the compounds used in this invention contain an asymmetric carbon atom. This invention is not limited to any particular isomer but includes the individual enantiomers as well as the racemates of the compounds.

Furthermore, it will be recognized that the compounds of the above formula, which are drawn as 4-substituted imidazoles, exist in equilibrium with the corresponding 5-substituted imidazole tautomers, and that a reference to the compounds used in this invention embodies both of these tautomers. The compounds are therefore referred to as 4(5)-substituted imidazoles.

The pharmaceutically acceptable acid addition salts of the compounds used in this invention can be prepared employing those acids of sufficient acidity to form acid addition salts with the imidazole group. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

In order to illustrate the preparation of the novel compounds of this invention, the following examples are provided. The examples are illustrative only and are not intended to limit the invention in any way.

EXAMPLE 1

α,α-Diphenylimidazole-4-propionamide hydrochloride

A solution of α,α-diphenylimidazole-4-propionitrile in 5 ml of 90% sulfuric acid was heated on a steam bath for 3.5 hours. The solution was poured over ice, basified with sodium hydroxide, and extracted with chloroform. The chloroform extract was evaporated to dryness, and the residue was dissolved in ethanol and treated with hydrogen chloride gas. The solution was evaporated and the residue was crystallized twice from acetonitrile/ethyl acetate to provide 1.058 g of the desired title product, m.p. 235°–238° C. with decomposition.

Analysis for $C_{18}H_{17}N_3O \cdot HCl$: Calculated: C, 65.95; H, 5.53; N, 12.82; Found: C, 65.77; H, 5.66; N, 12.75.

EXAMPLE 2

α,α-Bis(4-chlorophenyl)-1H-imidazole-4(5)-propionamide hydrochloride

Following the procedure of Example 1, 1.45 g of α,α-bis(4-chlorophenyl)imidazole-4(5)-propionitrile were heated with 6 ml of 90% sulfuric acid to provide 1.46 g of the desired title product, m.p. 254°–258° C. with decomposition.

Analysis for $C_{18}H_{15}Cl_2N_3O \cdot HCl$: Calculated: C, 54.50; H, 4.07; N, 10.59; Found: C, 54.45; H, 4.28; N, 10.39.

EXAMPLE 3

4(5)-(2,2-Diphenylethyl)imidazole

To a solution of 3.0 g of α,α-diphenylimidazole-4(5)-propionitrile in 25 ml of toluene were added in a dropwise fashion 15.27 ml of a 2.88M etherial solution of ethyl magnesium bromide. Thirty milliliters of tetrahydrofuran were added and the resulting solution was heated at reflux for about 20 hours. The reaction mixture was treated with 25 ml of 6N hydrochloric acid and allowed to reflux an additional 2 hours. The layers were separated, the aqueous layer was treated with base, and the solution was extracted with ether. The ether extract was dried over magensium sulfate and evaporated to dryness. The residue was crystallized twice from ethyl acetate to provide 0.53 g of the desired title product, m.p. 154.5°–156.5° C.

Analysis for $C_{17}H_{16}N_2$: Calculated: C, 82.22; H, 6.49; N, 11.28; Found: C, 82.10; H, 6.54; N, 11.13.

The compounds used in the method of this invention are useful in preventing or therapeutically treating estrogen-dependent diseases, including breast cancer, in mammals by virtue of thier ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-$H_2O$ which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity ($EC_{50}$) when the concentration of substrate (andorstenedione) is 0.1 μM. The $EC_{50}$'s of certain of the compounds of the above formula are summarized in Table 1.

TABLE 1

| Aromatase Inhibition in the Rat Ovarian Microsome Assay | |
|---|---|
| Compound | $EC_{50}$* |
| α-phenyl-α-(4-trifluoromethylphenyl)-1H—imidazole-4(5)-propionitrile | 0.073 |
| α-[1-imidazol-4(5)-ylmethyl]-α-phenyl-3-pyridineacetonitrile dihydrochloride | 0.56 |
| α-(4-chlorophenyl)-α-phenyl-imidazole-4(5)-propionitrile, maleic acid salt | 0.072 |
| α,α-bis(4-chlorophenyl)-imidazole-4(5)-propionitrile, maleic acid salt | 0.062 |
| α,α-bis(4-chlorophenyl)-1H—imidazole-4(5)-propanamide hydrochloride | <0.05 |
| α-(3-chlorophenyl)-α-phenyl-imidazole-4(5)-propionitrile hydrochloride | 0.078 |
| α-(4-methoxyphenyl)-α-phenyl-imidazole-4(5)-propionitrile, | 0.18 |

TABLE 1-continued

| Aromatase Inhibition in the Rat Ovarian Microsome Assay | |
| --- | --- |
| Compound | EC$_{50}$* |
| maleic acid salt | |
| 4(5)-(2,2-diphenylethyl)imidazole | 0.094 |
| α,α-diphenylimidazole-4(5)-propionitrile, maleic acid salt | 0.165 |
| α,α-diphenylimidazole-4(5)-propionamide hydrochloride | 0.118 |

*Concentration of compound in μM required to achieve 50% inhibition of aromatase activity when substrate concentration is 0.1 μM.

By virtue of their ability to inhibit the enzyme aromatase, the compounds to be employed in the method of this invention are able to inhibit the synthesis of estrogens in mammals, thereby making the compounds useful in the treatment of estrogen-dependent diseases, such as breast cancer. This in vivo activity was demonstrated in the following test systems.

Estrogen Synthesis Inhibition in Rats

Immature female Wistar rats (45–55 grams) were divided into control and test groups of 4–8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM MgCl$_2$·6H$_2$O, 320 mM sucrose, and 0.25% Triton X-100 (polyethylene glycol p-isooctyl phenyl ether, Rohm and Hass) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded and the pellet was dissolved in 0.3N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

TABLE 2

| Test No. | Compound | Effects of Compounds on estrogen levels and uterine weight | | | | | |
| --- | --- | --- | --- | --- | --- | --- | --- |
| | | Dose* | Animals | Mean Uterine Weight (mg) | Mean Steroid Concentration** | | |
| | | | | | estradiol | estrone | estriol |
| I | α,α-bis(4-chlorophenyl)-imidazole-4(5)-propionitrile, maleic acid salt | 30 | 4 | 166.0 | 1.36 | 0.11 | 0.72 |
| | | 300 | 5 | 141.6+ | 1.06 | 0.00+ | 0.23 |
| | testosterone-treated control | — | 8 | 196.1 | 2.77 | 0.30 | 0.94 |
| | Corn oil control | — | 6 | 107.0+ | — | — | — |
| II | α-phenyl-α-(4-trifluoromethylphenyl)-1H—imidazole-4(5)-propionitrile | 200 | 5 | 142.2+ | 1.01 | 0.00 | 0.31 |
| | Testosterone-treated control | — | 8 | 213.5 | 1.98 | 0.24 | 0.14 |
| | Corn oil control | — | 4 | 145.3+ | — | — | — |

*ppm in feed. 300 ppm corresponds to approximately 30 mg/kg/day; 200 ppm corresponds to approximately 20 mg/kg/day; 30 ppm corresponds to approximately 3 mg/kg/day.
**femtomoles per milligram of protein.
+significantly different from testosterone-treated control, p < 0.05.

DMBA-induced Mammary Tumor Inhibition

Mammary tumors were produced in female Sprague-Dawley rats which were 50–60 days old by the gavage administration of 20 mg of 7,12-dimethylbenz[α]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any othe group. Each control and test group contained 8 animals. The test compound was administered in corn oil and administered once daily by gavage.

Every experiment included a group of control rats having tumors that were given corn oil vehicle by gavage. The tumors were measured at the start of the experiments and generally had an area of approximately 15–100 $mm^2$. The area of each tumor was calculated by multiplying the shortest and longest diameters of the tumor. The treatment and measurement of animals continued for five weeks at which time the final areas of the tumors were determined. The change in the mean tumor area was determined, and the means change was analyzed for its significance using Dunnett's t-test. The results of these tests are shown in Table 3 below.

TABLE 3
Anti-Tumor Activity

| Test No. | Compound | Dose* | Duration of Test | Mean Tumor Area ($mm^2$) Start | Finish |
|---|---|---|---|---|---|
| I | Control | — | 5 weeks | 78.3 | 980.8 |
|   | α,α-bis(4-chlorophenyl)-imidazole-4(5)-propionitrile, maleic acid salt | 20 mg/kg | | 67.0 | 389.7+ |

+statistically different from control, $p < 0.05$.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Accordingly, the invention includes a pharmaceutical composition comprising as active ingredient a compound of the above formula associated with a pharmaceutically acceptable carrier. In making the compositions of the present invention, the active ingredient will usually be mixed with a carrier, or diluted by a carrier, or enclosed within a carrier which may be in the form of a capusle, sachet, paper or other container. When the carrier serves as a diluent, it may be a solid, or liquid material which acts as a vheicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions of the invention may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, by lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 4

Hard gelatin capsules are prepared using the following ingredients:

| | per capsule |
|---|---|
| α-(1-imidazol-4(5)-ylmethyl)-α-(4-chlorophenyl)-3-pyridine-acetonitrile | 250 mg |
| Starch dried | 200 mg |
| Magnesium stearate | 10 mg |

-continued

|  | per capsule |
|---|---|
| Total | 460 mg |

The above ingredients are mixed and filled into hard gelatin capsules in 460 mg quantities.

EXAMPLE 5

Capsules each containing 20 mg of medicament are made as follows:

|  | per capsule |
|---|---|
| α,α-bis(4-trifluoromethyl-phenyl)-imidazole-4(5)-propionitrile | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 6

Capsules each containing 100 mg of active ingredient are made as follows:

|  | per capsule |
|---|---|
| α-(2,4-difluorophenyl)-α-(4-chlorophenyl)-imidazole-4(5)-propionitrile | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 7

Tablets each containing 10 mg of active ingredient are made up as follows:

|  | per tablet |
|---|---|
| α,α-diphenylimidazole-4(5)-propionitrile | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 8

A tablet formula is prepared using the ingredients below:

|  | per tablet |
|---|---|
| α-(4-methoxyphenyl)-α-(4-methylphenyl)-imidazole-4(5)-propionitrile | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 9

Suppositories each containing 25 mg of active ingredient are made as follows:

|  | per suppository |
|---|---|
| α-(4-chlorophenyl)-α-(4-bromophenyl)-imidazole-4(5)-propionitrile | 25 mg |
| Saturated fatty acid glycerides to | 2,000 mg |

The active ingredient is passed through a No. 60 mesh U.S. sieve and suspended in the saturated fatty acid glycerides perviously melted using the minimum heat necessary. The mixture is then poured into a suppository mold of nominal 2 g capacity and allowed to cool.

EXAMPLE 10

Suspensions each containing 5 mg of medicament per 5 ml dose are made as follows:

|  | per 5 ml of suspension |
|---|---|
| α-[1-imidazol-4(5)-ylmethyl]-α-(3,4-dichlorophenyl)-3-pyridineacetonitrile | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 11

An aerosol solution is prepared containing the following components:

|  | Weight % |
|---|---|
| α,α-bis(2,4-dichlorophenyl)-imidazole-4(5)-propionitrile | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula

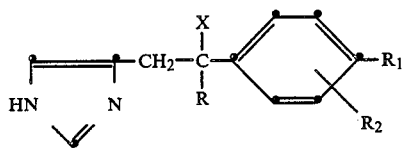

wherein
R is pyridyl or

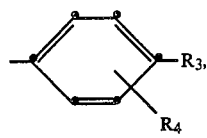

X is —CN, —CONH$_2$, or hydrogen, and
R$_1$, R$_2$, R$_3$, and R$_4$ are independently hydrogen, methyl, methoxy, fluoro, chloro, bromo, or trifluoromethyl,
or a pharmaceutically acceptable salt thereof.

2. The method according to claim 1 employing a compound wherein R is

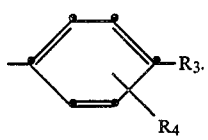

3. The method according to claim 2 employing a compound wherein R$_1$ and R$_3$ are independently chloro, fluoro, or trifluoromethyl.

4. The method according to claim 3 employing α,α-bis(4-chlorophenyl)imidazole-4(5)-propionitrile or a pharmaceutically acceptable salt thereof.

5. A method of treating estrogen-dependent diseases in a mammal which comprises administering to said mammal an effective amount of a compound according to the formula

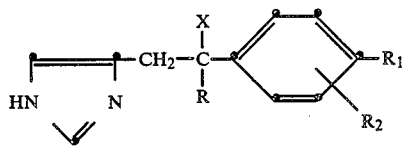

wherein
R is pyridyl or

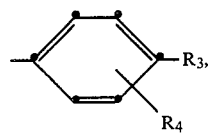

X is —CN, —CONH$_2$, or hydrogen, and
R$_1$, R$_2$, R$_3$, and R$_4$ are independently hydrogen, methyl, methoxy, fluoro, chloro, bromo, or trifluoromethyl,
or a pharmaceutically acceptable salt thereof.

6. The method according to claim 5 employing a compound wherein R is

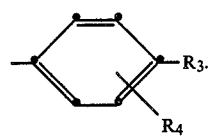

7. The method according to claim 6 employing a compound wherein R$_1$ and R$_3$ are independently chloro, fluoro, or trifluoromethyl.

8. The method according to claim 7 employing α,α-bis(4-chlorophenyl)imidazole-4(5)-propionitrile or a pharmaceutically acceptable salt thereof.

9. The method according to claim 5 wherein the estrogen-dependent disease is breast cancer.

10. The method according to claim 9 employing a compound wherein R is

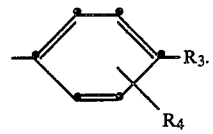

11. The method according to claim 10 employing a compound wherein R$_1$ and R$_3$ are independently chloro, fluoro, or trifluoromethyl.

12. The method according to claim 11 employing α,α-bis(4-chlorophenyl)imidazole-4(5)-propionitrile or a pharmaceutically acceptable salt thereof.

13. A pharmaceutical composition in unit dosage form useful to treat an estrogen-dependent disease in mammals which comprises from about 1 to about 500 mg of a compound of the formula

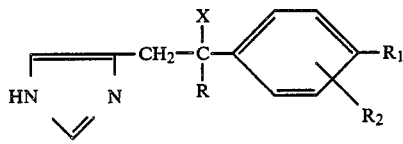

wherein
R is pyridyl or

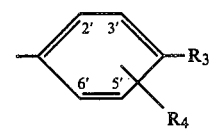

X is —CONH$_2$, and $R_1$, $R_2$, $R_3$, and $R_4$ are independently hydrogen, methyl, methoxy, fluoro, chloro, bromo, or trifluoromethyl, or a pharmaceutically acceptable salt thereof in combination with suitable pharmaceutical carriers, diluents, or excipients therefor.

14. A composition according to claim 13 employing a compound wherein R is

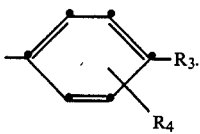

15. A composition according to claim 14 employing a compound wherein $R_1$ and $R_3$ are independently chloro, fluoro, or trifluoromethyl.

16. A compound of the formula

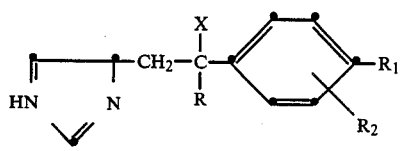

wherein

R is pyridyl or

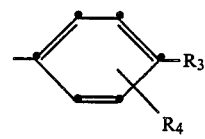

X is —$CONH_2$, and $R_1$, $R_2$, $R_3$, and $R_4$ are independently hydrogen, methyl, methoxy, fluoro, chloro, bromo, or trifluoromethyl, or a pharmaceutically acceptable salt thereof.

17. A compound according to claim 16 wherein R is

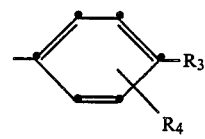

and $R_1$ and $R_3$ are independently chloro, fluoro, or trifluoromethyl.

18. The compound of claim 17 which is α,α-bis(4-chlorophenyl)-1H-imidazole-4(5)-propanamide or a pharmaceutically acceptable salt thereof.

* * * * *